United States Patent [19]

Flynn

[11] Patent Number: 5,635,502
[45] Date of Patent: Jun. 3, 1997

[54] MERCAPTOACETYLAMIDE BICYCLIC LACTAM DERIVATIVES USEFUL AS INHIBITORS OF ENKEPHALINASE AND ACE

[75] Inventor: Gary A. Flynn, Cincinnati, Ohio

[73] Assignee: Merrell Pharmaceuticals Inc., Cincinnati, Ohio

[21] Appl. No.: 406,979

[22] PCT Filed: Sep. 23, 1993

[86] PCT No.: PCT/US93/09001

§ 371 Date: Apr. 3, 1995

§ 102(e) Date: Apr. 3, 1995

[87] PCT Pub. No.: WO94/10193

PCT Pub. Date: May 5, 1994

Related U.S. Application Data

[63] Continuation-in-part of Ser. No. 968,770, Oct. 30, 1992, abandoned.

[51] Int. Cl.[6] .................. A61K 37/64; A61K 31/55; C07K 5/06; C07D 223/10; C07D 498/02
[52] U.S. Cl. ................. 514/214; 540/485; 540/490; 540/497; 540/521; 540/523; 540/491; 514/211; 514/215
[58] Field of Search ................. 514/214, 211, 514/215; 540/485, 490, 491, 497, 521, 523

[56] References Cited

U.S. PATENT DOCUMENTS

| | | | |
|---|---|---|---|
| 3,334,091 | 8/1967 | Houlihan | 540/521 X |
| 3,334,095 | 8/1967 | Houlihan | 540/521 X |
| 4,080,449 | 3/1978 | Croisier et al. | 424/244 |
| 4,320,057 | 3/1982 | Freed et al. | 540/490 |
| 4,391,752 | 7/1983 | Crossley | 540/490 |
| 4,399,136 | 8/1983 | Hassall et al. | 424/250 |
| 4,415,496 | 11/1983 | Harris et al. | 424/258 X |
| 4,487,929 | 12/1984 | Hassall et al. | 544/224 |
| 4,512,924 | 4/1985 | Attwood et al. | 544/235 X |
| 4,584,294 | 4/1986 | Ruyle | 514/214 |
| 4,658,024 | 4/1987 | Attwood et al. | 540/400 |
| 4,692,438 | 9/1987 | Hassall et al. | 514/183 |
| 4,716,232 | 12/1987 | Temansky | 548/112 |
| 4,734,504 | 3/1988 | Holmes | 548/130 X |
| 4,734,505 | 3/1988 | Holmes | 544/182 X |
| 4,762,924 | 8/1988 | Hassall et al. | 540/501 |
| 4,772,701 | 9/1988 | Attwood et al. | 544/235 |
| 4,782,149 | 11/1988 | Lawton et al. | 540/500 |
| 4,785,093 | 11/1988 | Hassall et al. | 540/460 |
| 4,808,713 | 2/1989 | Attwood et al. | 540/487 |
| 4,824,832 | 4/1989 | Flynn et al. | 514/214 |
| 4,826,980 | 5/1989 | Hassall et al. | 544/224 |
| 4,973,585 | 11/1990 | Flynn et al. | 514/214 |
| 5,208,230 | 5/1993 | Flynn et al. | 514/214 |
| 5,238,932 | 8/1993 | Flynn et al. | 514/214 |
| 5,362,727 | 11/1994 | Robl | 514/214 |

FOREIGN PATENT DOCUMENTS

| | | | |
|---|---|---|---|
| 0128728 | 12/1984 | European Pat. Off. | 514/214 |
| 0249223 | 12/1987 | European Pat. Off. | 514/214 |
| 0249224 | 12/1987 | European Pat. Off. | 514/214 |
| 0322914 | 12/1988 | European Pat. Off. | 514/214 |
| 0481522 | 4/1992 | European Pat. Off. | 514/214 |
| 0492369 | 7/1992 | European Pat. Off. | 514/214 |
| 0533084 | 9/1992 | European Pat. Off. | 540/400 |
| 0559444 | 5/1993 | European Pat. Off. | 514/214 |
| 9108195 | 6/1991 | WIPO | 514/214 |
| 9109840 | 7/1991 | WIPO | 514/214 |
| 9302099 | 2/1993 | WIPO | 514/214 |

OTHER PUBLICATIONS

Flynn, et al., J. Am. Chem. Soc. 109, 7914 (1987).
Flynn, et al., Peptide Chemistry (1987); T. Shiba & Sakakibara (ed.), Protein Research Foundation, Osaka (1988).
Flynn, et al., Tetrahedron Letters, vol. 31 (6), 815–88 (1990).
Attwood, et al., J. Chem. Soc. Perkin Trans. I, pp. 1011–1019 (1986).
Natoff, et al., Drugs of the Future, vol. 12 (5): 475–483 (1987).

(List continued on next page.)

*Primary Examiner*—Floyd D. Higel
*Attorney, Agent, or Firm*—Charlotte L. Barney

[57] ABSTRACT

The present invention relates to certain novel mercaptoacetylamide bicyclic lactam derivatives useful as inhibitors of enkephalinase and of ACE.

These mercaptoacetylamide bicyclic lactam derivatives can be described by the following formula:

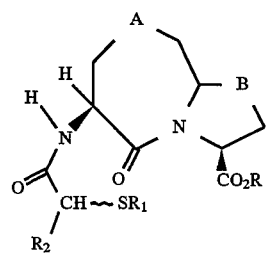

wherein

R is hydrogen, a $C_1$-$C_4$ alkyl, an Ar—Y—group, —$CH_2O$—$C(O)C(CH_3)_3$ or diphenylmethyl;

$R_1$ is hydrogen, acetyl, —$CH_2O$—$C(O)C(CH_3)_3$, benzoyl or a group of the formula

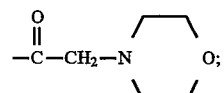

$R_2$ is hydrogen, $C_1$-$C_8$ alkyl, —$CH_2OCH_2CH_2OCH_3$ or an Ar—Y—group;

A is —$CH_2$—, —O—, or —S—;

B is —S— or —O—; and pharmaceutically acceptable salts thereof.

32 Claims, No Drawings

OTHER PUBLICATIONS

J. Med. Chem. 1992, 35, 823–832, Timothy D. Ocain et al.

Fournie–Zaluski, Marie–Claude et al., *J. Med. Chem.*, 1992 vol. 35, pp. 2473–2481.

Fournie–Zaluski, Marie–Claude et al., II *J. Med. Chem.*, 1992 vol. 35, pp. 1259–1266.

French, John F., *Jour. of Pharm and Exper. Therapeutics*, vol. 268, No. 1, pp. 180–18.6 (1994).

Powell Jerry S. et al., *Journal of American College of Cardiology*, vol. 17, No. 6, pp. 137B–142B (May 1991).

Davis, Harry R. et al., *Supplement I Circulation*, vol. 86, No. 4 p. I–220(0873), (Oct. 1992).

Burkholder, et al. *Bioorganic and Medical Chem. Letters*, vol. 3, No. 2, pp. 231–234, 1993.

Flynn et al., *J. Med. Chem.* 1993, 36 2420–2423.

*Bioorganic and Medical Chem. Letters*, vol. 1, 309, 1991.

MERCAPTOACETYLAMIDE BICYCLIC LACTAM DERIVATIVES USEFUL AS INHIBITORS OF ENKEPHALINASE AND ACE

This is a continuation-in-part of application Ser. No. 07/968,770, filed Oct. 30, 1992 now abandoned.

BACKGROUND OF THE INVENTION

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome ANP refers to a family of naturally-occurring peptides which are involved in the homeostatic regulation of blood pressure, as well as sodium and water levels. ANP have been found to vary in length from about 21 to about 126 amino acids with a common structural feature being one or more disulfide-looped sequences of 17 amino acids with various amino- and carboxy-terminal sequences attached to the cystine moiety. ANP have been found to bind to specific binding sites in various tissues including kidney, adrenal, aorta, and vascular smooth muscle with affinities ranging from about 50 pico-molar (pM) to about 500 nano-molar (nM) [Needleman, *Hypertension* 7, 469 (1985)]. In addition, it is believed that ANP binds to specific receptors in the brain and possibly serves as a neuromodulator as well as a conventional peripheral hormone.

The biological properties of ANP involve potent diuretic/ natriuretic and vasodilatory/hypotensive effects as well as an inhibitory effect on renin and aldosterone secretion [deBold, *Science* 230, 767 (1985)]. By inhibiting enkephalinase, the metabolic degradation of the naturally-occurring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension,, renal diseases, hyperaldosteronemia, cardiac hypertrophy, glaucoma and congestive heart failure.

In addition, the compounds of the present invention are inhibitors of Angiotension-Converting Enzyme (ACE). ACE is a peptidyl dipeptidase which catalyzes the conversion of angiotensin I to angiotensin II. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides—Angiotensin, Plasma Kinins, and Others", Chapter 27, in GOODMAN AND GILLMAN'S THE PHARMACOLOGICAL BASIS OF THERAPEUTICS, 7th edition, 1985, pp. 652–3, MacMillan Publishing Co., New York, N.Y.]. In addition, it has been discovered that ACE inhibitors are useful in treating cognitive disorders [German Application No. 3901-291-A, published Aug. 3, 1989].

Bradykinin refers to a naturally-occurring peptide which is a very powerful vasodilator causes increased capillary permeability. By inhibiting enkephalinase and ACE, the metabolic degradation of bradykinin is inhibited, thereby providing increased levels of bradykinin in the circulation.

In addition, the compounds of the present invention are useful as inhibitors of smooth cell proliferation. Smooth muscle cell proliferation in the intima of muscular arteries is a primary cause of vascular stenosis in arteriosclerosis, after vascular surgery, and after coronary angioplasy. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J. S., Muller, R. K. M. and Baumgartner, H. R.; Suppression of the vascular response to injury: The role of angiotensin-converting enzyme inhibitors. J. Am. Coll. Cardiol. 17:137B-42B, 1991. More recently, artial natruiuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D. C. Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis Sybertz, European Patent Application 533084-A1, Mar. 24, 1993.

European Patent Application 0 481 522 A1 (Apr. 22, 1992) describes novel mercaptoacetylamide derivatives useful as inhibitors of enkephalilnase and ACE; Biochemical and Biophysical Research Communications, Vol. 117(1), 1983, pages 108–113 describes inhibitors of ACE derived from benzofused 1-carboxyalkyl-3-(1-carboxy-3-phenylpropylamino)lactams; and European Patent Application 0 240 366 (Oct. 7, 1987) describes perhydrothiazepine and perhydroazepine derivatives useful as inhibitors of ACE.

SUMMARY OF THE INVENTION

The present invention provides novel compounds of the Formula (I)

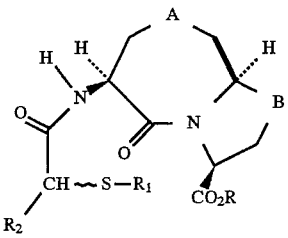

(I)

wherein

R is hydrogen, a $C_1$–$C_4$ alkyl or an Ar—Y— group, —$CH_2$O—C(O)C($CH_3$)$_3$ or diphenylmethyl;

$R_1$ is hydrogen, acetyl, —$CH_2$O—C(O)C($CH_3$)$_3$ or benzoyl or a group of the formula

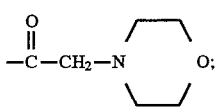

$R_2$ is hydrogen, $C_1$–$C_8$ alkyl, —$CH_2OCH_2CH_2OCH_3$ or an Ar—Y— group;

A is —$CH_2$—, —O—, or —S—;

B is —S— or —O—; and and the pharmaceutically acceptable salts thereof.

The present invention further provides a method of inhibiting enkephalinase in a patient in need thereof comprising administering to said patient an effective enkephalinase inhibitory amount of a compound of Formula (I). The present invention also provides a method of inhibiting ACE in a patient in need thereof comprising administering to said patient an effective ACE inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used herein, the term "$C_1$–$C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The term "$C_1$–$C_4$ alkyl" refers to a saturated straight or branched chain hydrocarboxy radical of one to four carbon atoms and includes methoxy, ethoxy, propoxy, isopropoxy, n-butoxy, isobutoxy, tertiary butoxy and the like.

As used herein, the term "Ar—Y—" refers to a radical wherein Ar is an aryl group and Y is a $C_0$–$C_4$ alkyl. The term "Ar" refers to a phenyl, 2-benzofuranyl or naphthyl group unsubstituted or substituted with from one to three substituents selected from the group consisting of methylenedioxy, hydroxy, $C_1$–$C_4$ alkoxy, fluoro and chloro. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Y—" are phenyl, naphthyl, phenylmethyl or benzyl, phenylethyl, p-methoxybenzyl, 3,4-methylenedioxy, p-fluorobenzyl and p-chlorobenzyl.

As used herein, the designation "〰" refers to a bond to a chiral atom for which the stereochemistry is not designated.

Compounds of Formula (I) can form pharmaceutically acceptable salts with any non-toxic, organic or inorganic acid. Illustrative inorganic acids which form suitable salts include hydrochloric, hydrobromic, sulphuric and phosphoric acid and acid metals salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salacylic, 2-phenoxybenzoic and sulfonic acids such as methane sulfonic, trifluoromethane sulfonic, 2-hydroxyethane sulfonic acid and p-toluenesulfonic acid.

The compounds of Formula (I) can be prepared by utilizing procedures and techniques well known and appreciated by one of ordinary skill in the art. A general synthetic scheme for preparing these compounds is set forth in Scheme A wherein all substituents, unless other indicated, are as previously defined.

Scheme A

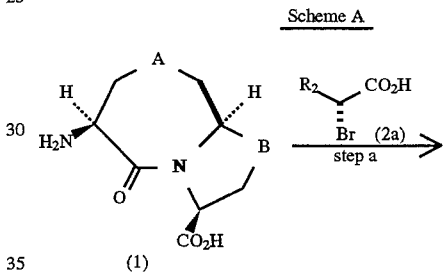

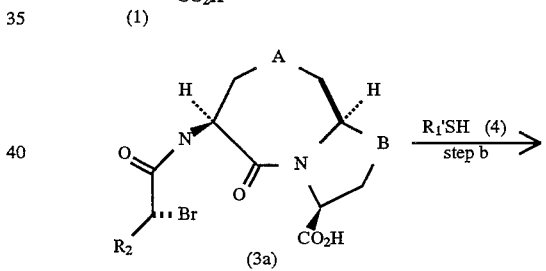

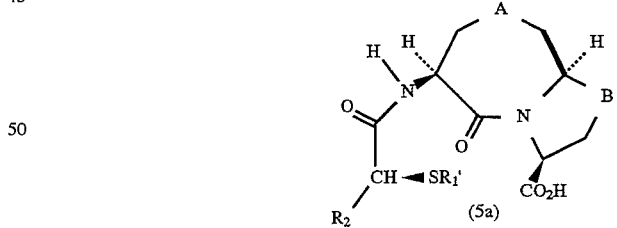

$R_1' = COCH_3$ or COPh

In step a, the appropriate bicyclic lactam compound of structure (1) is reacted with the appropriate (S)-bromoacid of structure (2a) to give the corresponding (S)-bromoamide compound of structure (3a). For example, the appropriate bicyclic lactam compound of structure (1) can be reacted with the appropriate (S)-bromoacid of structure (2a) in the presence of a coupling reagent such as EEDQ (1-ethoxycarbonyl-2-ethoxy-1,2-dihydroquinoline), DCC (1,3-dicyclohexylcarbodiimide), or diethylcyanophosponate in a suitable aprotic solvent, such as methylene chloride to give the appropriate (S)-bromoamide compound of structure (3a).

Alternatively the appropriate bicyclic lactam compound of structure (1) is reacted with the appropriate (R)-bromoacid to give the corresponding (R)-bromoamide or the appropriate bicyclic lactam compound of structure (1) is reacted with the appropriate enantiomeric mixture of the bromoacid to give the corresponding enantiomeric mixture of bromoamide as described.

In step b, the (S)-bromo functionality of the appropriate (S)-bromoamide compound of structure (3a) is converted to the corresponding (R)-thioacetate or (R)-thiobenzoate of structure (5a).

For example, the appropriate (S)-bromoamide compound of structure (3a) is reacted with thiolacetic acid or thiolbenzoic acid of structure (4) in the presence of a base, such as cesium carbonate. The reactants are typically contacted in a suitable organic solvent such as a mixture of dimethylformamide and tetrahydrofuran. The reactants are typically stirred together at room temperature for a period of time ranging from 1 to 8 hours. The resulting (R)-thioacetate or (R)-thiobenzoate of structure (5a) is recovered from the reaction zone by extractive methods as is known in the art. It may be purified by chromatography.

Alternatively, the (R)-bromo functionality of the appropriate (R)-bromoamide is converted to the corresponding (S)-thioacetate or (S)-thiobenzoate or the bromo functionality of the appropriate enantiomeric mixture of the bromoamide wherein is converted to the corresponding enantiomeric mixture of thioacetate or thiobenzoate compounds.

As summarized in Table 1, the R and $R_1$ groups on the compounds of structures (5) can be manipulated using techniques and procedures well known and appreciated by one of ordinary skill in the art to give the corresponding compounds of structures (6)–(12).

The (R)-thioacetate or (R)-thiobenzoate functionality of the appropriate compound of structure (5) can be removed with lithium hydroxide in a suitable solvent mixture such as tetrahydrofuran and ethanol to give the appropriate (R)-thio compound of structure (6).

Alternatively, the carboxylic acid functionality of the appropriate compound of structure (5) can be re-esterified using techniques and procedures well known and appreciated in the art. For example, a compound of structure (7) can be prepared by treating the carboxylic acid compound of structure (5) with the appropriate alkyl halide in a suitable aprotic solvent, such as dimethylformamide along with a non-nucleophilic base, such as cesium carbonate.

The (R)-thioacetate or (R)-thiobenzoate functionalities of the appropriate compounds of structure (7) can be hydrolyzed to the corresponding (R)-thiol compounds of structure (8) with ammonia in a suitable protic solvent, such as methanol.

The thiol functionality of the appropriate compound of structure (6) can be alkylated using techniques and procedures well known and appreciated in the art. For example, a compound of structure (9) can be prepared by treating the thiol compound of structure (6) with chloromethyl pivalate in a suitable aprotic solvent, such as dimethylformamide along with a non-nucleophilic base, such as cesium carbonate or pyridine.

The thiol functionality of the appropriate compound of structure (8) can be alkylated using techniques and procedures well known and appreciated in the art. For example, a compound of structure (10) can be prepared by treating the thiol compound of structure (8) with chloromethyl pivalate as described above for the conversion of (6) to (9).

The thiol functionality of the appropriate compound of structure (6) can be acylated to give the 4-morpholinoacetyl compound of structure (11). For example, a compound of structure (11) can be prepared by treating the thiol compound of structure (6) with 4-morpholinethiolacetate in the presence of a coupling reagent such as DCC in a suitable aprotic solvent such as methylene chloride.

In addition, a 4-morpholinoacetyl compound of structure (11) can be prepared by treating the (R) or (S)-bromoamide compound of structure (3) wherein with triphenylmethyl 4-morpholinethiolacetate in the presence of a base, such as sodium hyride, in a suitable aprotic solvent such as dimethylformamide.

The thiol functionality of the appropriate compound of structure (8) can acylated to give the 4-morpholinoacetyl compound of structure (12). For example, a compound of structure (12) can be prepared by treating the thiol compound of structure (8) with 4-morpholinethiolacetate in the presence of a coupling reagent such as DCC in a suitable aprotic solvent such as methylene chloride.

TABLE 1

| MANIPULATION OF R AND $R_1$ | | |
|---|---|---|
| Compound | R | $R_1$ |
| 5 | H | $COCH_3$ or COPh |
| 6 | H | H |
| 7 | $C_1$-$C_4$ alkyl, Ar—Y, —$CH_2OCOC(CH_3)_3$, diphenylmethyl | $COCH_3$ or COPh |
| 8 | $C_1$-$C_4$ alkyl, Ar—Y, —$CH_2OCOC(CH_3)_3$, diphenylmethyl | H |
| 9 | H | —$CH_2OCOC(CH_3)_3$ |
| 10 | $C_1$-$C_4$ alkyl, Ar—Y, —$CH_2OCOC(CH_3)_3$, diphenylmethyl | —$CH_2OCOC(CH_3)_3$ |
| 11 | H | 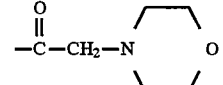 |
| 12 | $C_1$-$C_4$ alkyl, Ar—Y, —$CH_2OCOC(CH_3)_3$, diphenylmethyl | 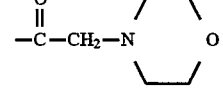 |

Starting materials for use in the general synthetic procedures outlined in Scheme A are readily available to one of ordinary skill in the art. For example, [3R-(3α,6α,9aβ)-6-aminooctahydro-5-oxo-thiazolo[3,2-a]azepine-3-carboxylic acid may be prepared as described in U.S. Pat. No. 4,415,496 (Nov. 15, 1983).

Alternatively, the bicyclic lactam starting materials of structure (1) may be prepared as set forth in Scheme B. In Scheme B, all substituents are as previously described unless otherwise indicated.

7

Scheme B

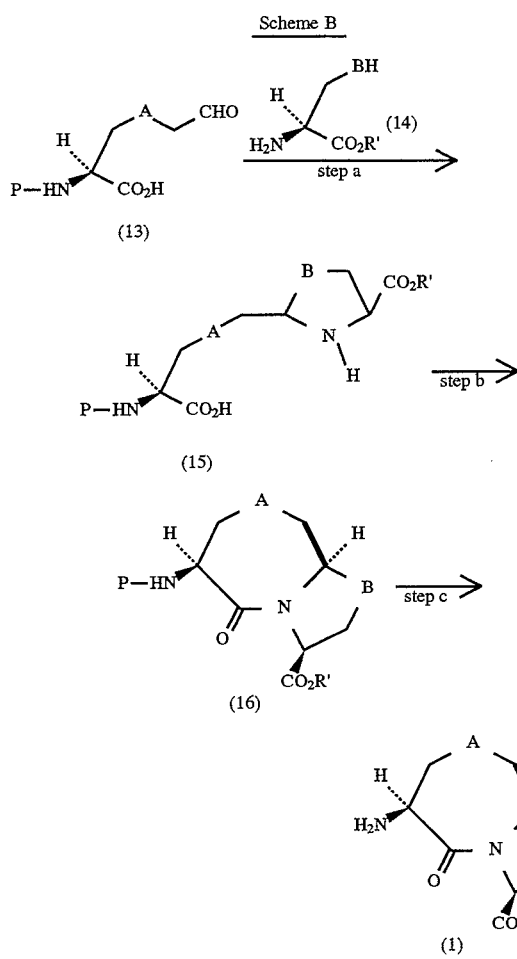

P = Boc, CBZ or Phth
R' = Me or Et

In step a, the aldehyde compound of structure (13) is condensed with an ester of L-serine or L-cysteine (14) to give a diastereomeric mixture of oxazolidines or thiazolidines of structure (15).

In step b, the diastereomeric mixture of oxazolidines or thiazolidines of structure (15) is cyclized with N-ethoxycarbonyl-2-ethoxy-1,2-dihydroquinoline to form the protected (S,R,R) and (S,S,R) bicyclic lactams. The protected bicyclic lactams are then separated to give the protected bicyclic lactam of structure (16).

In step c, the protected bicyclic lactam of structure (16) is deprotected to give the bicyclic lactam of structure (1).

Starting materials for use in Scheme B are readily available to one of ordinary skill in the art. For example, 5-formyl-2(S)-phthalimidopentanoic acid is described in U.S. Pat. No. 4,415,496 (Nov. 15, 1983).

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "µL" refers to microliters; "µg" refers to micrograms; and "µM" refers to micromolar.

8

EXAMPLE 1

[3R-[3α,6α,(S*),9aα]]-6-[[1-Oxo-2(S)-acetylthio-3-phenylpropyl]amino]octahydro-5-oxothiazolo[3-2-a][1,4]thiazepine-3-carboxylic acid

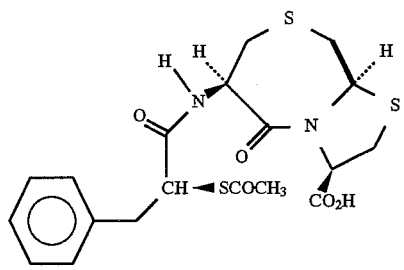

Scheme B, step a: Ethyl 2-[[[2'-carboxy-2'-benzoyloxycarbonyl]ethyl]ethylsulfide]-4(R)-thiazolidinecarboxylate Wash sodium hydride (7.75 g, 191 mmol of a 59% dispersion in paraffin) 2 times with dry hexane (2×) under a nitrogen atmosphere. Add anhydrous dimethylformamide (90 mL) and cool with an ice/methanol bath. A, by portionwise addition, L-cysteine ethyl ester hydrochloride (96.7 mmol), stir for 5 minutes and add potassium iodide (5.2 g, 32 mmol). Add, by dropwise addition, bromoacetaldehyde diethylacetal (14.5 mL, 96.7 mmol), remove the ice bath and stir for 8 hours at room temperature. Evaporate the solvent in vacuo to give S-(2-Diethoxyethyl)-L-cysteine ethyl ester which is used in the next step without purification.

Mix S-(2-Diethoxyethyl)-L-cysteine ethyl ester (6.6 mmol) and pyridine (60 mL). Add, by dropwise addition, benzyl chloroformate (7.3 mmol) and stir overnight. Remove excess pyridine in vacuo and dissolve the residue in a two-phase mixture of ethyl acetate/water. Separate the organic phase and extract the aqueous phase with additional ethyl acetate (2×). Wash the combined organic phases with water, then brine and dry (MgSO$_4$). Evaporate the solvent in vacuo to give N-(benzyloxycarbonyl)-S-(2-diethoxyethyl)-L-cysteine ethyl ester.

Dissolve N-(benzyloxycarbonyl)-S-(2-diethoxyethyl)-L-cysteine ethyl ester (21.7 mmol) in ethanol (150 mL. Add 1N lithium hydroxide (50 mL) and stir overnight at room temperature. Carefully adjust to pH 4 with 1N hydrochloric acid and stir for 1 hour. Extract into ethyl acetate, dry (MgSO$_4$) and evaporate the solvent in vacuo to give N-(benzyloxycarbonyl)-S-(formylmethyl)-L-cysteine.

Dissolve L-cysteine ethyl ester (12.7 mmol) in tetrahydrofurn (120 mL) and add N-(benzoyloxycarbonyl)-S-(formylmethyl)-L-cysteine (12.7 mmol). Place under a nitrogen atmosphere and stir for 3 hours. Evaporate the solvent in vacuo, dissolve the residue in chloroform and wash with water (2×30 mL). Combine the aqueous extracts and extract with chloroform (2×30 mL). Combine all organic extracts, dry (Na$_2$SO$_4$) and evaporate the solvent in vacuo to give the title compound.

Scheme B, step b: Ethyl [3R-[3α,6α,(S*),9aα]]-6-[benzyloxycarbonylamino]octahydro-5-oxothiazolo[3,2-a][1,4]thiazepine-3-carboxylate and Ethyl [3R-[3α, 6α, (S*), 9aβ]]-6-[benzyloxycarbonylamino]octahydro-5-oxothiazolo[3,2-a][1,4]thiazepine-3-carboxylate Dissolve ethyl 2-[[[2'-carboxy-2'-benzyloxycarbonyl]ethyl]ethylsulfide]-4(R)-thiazolidinecarboxylate (12.7 mmol) in tetrahydrofuran (30 mL) and add N-etoxycarbonyl-2-ethoxy-1,2-dihydroquinoline (EEDQ) (469 mg). Stir overnight at room temperature under a nitrogen atmosphere. Evaporate the solvent in vacuo, partition between ethyl acetate and dilute hydrochloric acid. Separate the organic phase, wash with 5% sodium bicarbonate solution, water and brine. Dry (Na₂SO₄), evaporate the solvent in vacuo and purify and separate the isomers by silica gel chromatography to dive the separate isomeric title compounds.

Scheme B, step c: [3R-[3α,6α,(S*),9aα]]-6-amino-octahydro-5-oxothiaxolo[3,2-a][1,4]thiazepine-3-carboxylic acid Dissolve ethyl [3R-[3α,6α,(S*),9aα]]-6-[benzyloxycarbonylamino]octahydro-5-oxothiazolo[3,2-a][1,4]thiaxepine-3-carboxylate (21.7 mmol) in ethanol (150 mL). Add 1N lithium hydroxide (50 mL) and stir overnight at room temperature. Concentrate in vacuo. Partition between ethyl acetate and 6N hydrochloric acid. Separate the organic phase and wash with brine. Dry (MgSO₄) and evaporate the solvent in vacuo to give [3R-[3α,6α,(S*),9aα]]-6-[benzyloxycarbonylamino]octahydro-5-oxothiazolo[3,2-a][1,4]thiazepine-3-carboxylic acid.

Mix [3R-[3α,6α,(S*),9aα]]-6-[benzyloxycarbonylamino]octahydro-5-oxothiazolo]3,2-a][1,4]thiazepine-3-carboxylic acid (27.7 mmol), trifluroacetic acid (75 mL) and anisole (5 mL). Stir at room temperature overnight. Pour onto water and carefully neutralize with solid sodium hydrogen carbonate. Extract into ethyl acetate (2×), wash with brine and dry (MgSO₄). Evaporate the solvent in vacuo and purify by chromatography to give the title compound.

Scheme A, step a: [3R-[3α,6α,(S*),9aα]]-6-[[1-Oxo-2(R)-bromo-3-phenylpropyl]amino]octahydro-5-oxothiazolo[3-2-a][1,4]thiazepine-3-carboxylic acid Mix D-phenylalanine (186.4 g, 1.128 mol) and 49% hydrobomic acid (372.8 g), cool to −5° C. and add, by dropwise addition, a solution of sodium nitrite (77.9 g) in water (565 mL) over a period of 1 hour (vigorous gas evolution). Stir at −5° C. to 0° C. for 4 hours, extract into ethyl ether (3×1L), dry (MgSO₄) and evaporate the solvent in vacuo. Purify by chromatography (5% acetic acid/95% methylene chloride) and distill to give 3-phenyl-2(R)-bromopropionic acid (112 g, 43%); bp 128°–135° C. @0.25 torr.

Mix 3-phenyl-2(R)-bromopropionic acid (1.0 mmol) and [3R-[3α,6α,(S*),9aα]]-6-amino-octahydro-5-oxothiazolo[3,2-a][1,4]thiazepine-3carboxylic acid (1.0 mmol) in methylene chloride (6 mL). Add EEDQ (247 mg, 1.0 mmol). Stir for 15 hours at ambient temperature under argon atmosphere. Dilute with ethyl acetate (25 mL) and wash with 5% sulfuric acid (15 mL), then saturated sodium hydrogen carbonate (15 mL). Dry (Na₂SO₄), concentratee in vacuo and purify by silica gel chromatography to yield the title compound.

Scheme A, step b: [3R-[3α,6α,(S*), 9aα]]-6-[[1-Oxo-2(S)-acetylthio-3-phenylpropyl]amino]octahydro-5-oxothiaxolo[3-2-a][1,4]thiaxepine-3-carboxylic acid Dissolve thioacetic acid (0.10 mL, 1.4 mmol) in methanol (5 mL) and treat with cesium carbonate (228 mg, 0.70 mmol). Stir the yellow solution for 30 minutes then evaporate the solvent in vacuo. Dilute the resulting cesium salt with dimethylformamdie (10 mL) and treat with a solution of [3R-[3α,6α,(S*),9aα]]-6-[[1-Oxo-2(R)-bromo-3-phenylpropyl]amino]octahydro-5-oxothiazolo[3-2-a][]1,4]thiazepine-3-carboxylic acid (1.0 mmol) in tetrahydrofurn (6 mL). Stir at room temperature for 2 hours, evaporate the solvent in vacuo and partition between ethyl acetate (75 mL) and brine (50 mL). Dry the organic phase (Na₂SO₄), evaporate the solvent in vacuo and purify by chromatography to give the title compound.

EXAMPLE 2

[3R-[3α,6α(S*),9aα]]-6-[[1-Oxo-2(S)-thio-3-phenypropyl]amino]octahydro-5-oxothiazolo[3-2-a][1,4]thiazepine-3-carboxylic acid Dissolve [[3R-[3α,6α,(S*),9aα]]-6-[[1-Oxo-2(S)-acetylthio-3-penylpropyl]amino]octahydro-5-oxothiazolo[3-2-a][1,4]thiazepine-3-carboxylic acid (0.145 mmol) in degassed

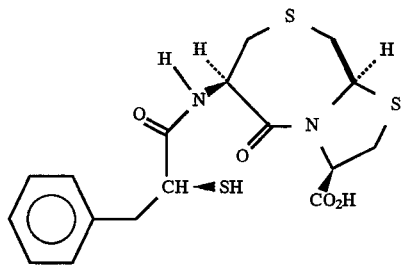

methanol (3 mL) and tetrahydrofuran (2 mL), cool in an ice bath and add lithium hydroxide (0.6 mL of a 1M solution, 0.6 mmol). Stir the reaction mixture for 3 hours and add 1N hydrochloric acid. Partition between methylene chloride (75 mL) and water (25 mL). Dry (Na₂SO₄), evaporate the solvent in vacuo and purify by chromatography to give the title compound.

EXAMPLE 3

[3R-[3α,6α,(S*),9aα]]-6-[[1-Oxo-2-(S)-(4-morpholino)acetylthio-3-phenylpropyl]amino]octahydro-5-oxothiazolo[3-2-a][1,4]thiazepine-3-carboxylic acid

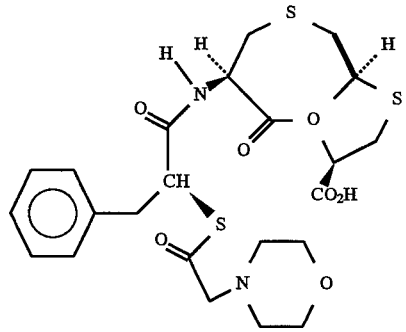

Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenymethyl 4-morpholinethiolacetate (1.61 g, 4.0 mmol) and heat gently for 1.5 hours while bubbling nitrogen through the solution to facilitate removal of excess hydrogen sulfide gas. Add [3R-[3α,6α,(S*),9aα]]-6-[[1-oxo-2(R)-bromo-3-phenypropyl]amino]octahydro-5-oxothiazolo[3-2-a][1,4]thiazepine-3-carboxylic acid (2.0 mmol) and stir for 2 hours. Pour into water, extract into ethyl acetate, wash with brine and dry (MgSO₄). Evaporate the solvent in vacuo and purify by chromatography to give the title compound.

EXAMPLE 4

[3R-[3α,6α,(S*),9aα]]-6-[[1-Oxo-2(S)-acetylthio-3-phenylpropyl]amino]octahydro-5-oxothiazolo[3-2-a][1,4]oxazepine-3-carboxylic acid

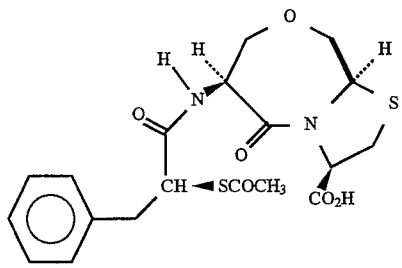

Scheme C, step a: Ethyl 2-[[[2'-carboxy-2'-benzoyloxycarbonyl]ethyl]ethylether]-4(R)-thiazolidinecarboxylate Mix L-serine methyl ester (6.6 mmol) and pyridine (60 mL). Add, by dropwise addition, benzyl chloroformate (7.3 mmol) and stir overnight. Remove excess pyridine in vacuo and dissolve the residue in a two-phase mixture of ethyl acetate/water. Separate the organic phase and extract the aqueous phase with additional ethyl acetate (2×). Wash the combined organic phases with water, then brine and dry (MgSO$_4$). Evaporate the solvent in vacuo to give N-(benzyloxycarbonyl)-L-serine methyl ester.

Dissolve N-(benzyloxycarbonyl)-L-serine methyl ester (63 mmol) in methylene chloride/cyclohexane (1:1, 600 mL). Add allyl trichloroacetimidate (26 g, 128 mmol) and trifluromethanesulfonic acid (5 mL, 56.6 mmol). Stir at room temperature under a nitrogen atmosphere for 5 hours and dilute with methylene chloride. Wash with saturated aqueous sodium hydrogen carbonate, water, dry (MgSO$_4$) and evaporate the solvent in vacuo. Purify by silica gel chromatography to give N-(benzyloxycarbonyl)-O-2-propenyl-L-serine methyl ester.

Dissolve N-(benzyloxycarbonyl)-O-2-propenyl-L-serine methyl ester (21.7 mmol) in ethanol (150 mL). Add 1N lithium hydroxide (50 mL) and stir overnight at room temperature. Reflux for 1 hour, cool to −10°, carefully adjust to pH 4 with 1N hydrochloric acid and stir for 1 hour. Extract into ethyl acetate, dry (MgSO$_4$) and evaporate the solvent in vacuo to give N-(benzyloxycarbonyl)-O-2-propenyl-L-serine.

Dissolve N-(benzyloxycarbonyl)-O-2-propenyl-L-serine (29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methylfulfide (12 mL, 0.164 mol) and allow to warm to room temperature. Stir at room temperature for 24 hours, evaporate the solvent in vacuo and dissolve the residue in ethyl acetate (220 mL). Wash with water, saturated sodium chloride, dry (MgSO$_4$) and evaporate the solvent in vacuo to give N-(benzyloxycarbonyl)-O-2-oxoethyl-L-serine methyl ester.

Dissolve L-cysteine ethyl ester (12.7 mmol) in tetrahydrofurn (120 mL) and add N-(benzyloxycarbonyl)-O-2-oxoethyl-L-serine methyl ester (12.7 mmol). Place under a nitrogen atmosphere and sitr for 3 hours. Evaporate the solvent in vacuo, dissolve the residue in chloroform and wash with water (2×30 mL). Combine the aqueous extracts and extract with chloroform (2×30 mL). Combine all organic extracts, dry (Na$_2$SO$_4$) and evaporate the solvent in vacuo to give the title compound.

Scheme B, step b: Ethyl [3R-[3α,6α,(S*),9aα]]-6-[benzyloxycarbonlamino]octahydro-5-oxothiazolo[3,2-a][1,4]oxazepine-3-carboxylate and Ethyl [3R-[3α,6α,(S*),9aβ]]-6-[benzyloxycarbonylamino]octahydro-5-oxothiazolo[3,2-a][1,4]oxazepine-3-carboxylate Dissolve ethyl 2-[[[2'-carboxy-2'-benzyloxycarbonyl]ethyl]ethylether]-4(R)-thiazolidinecarboxylate (12.7 mmol) in tetrahydrofuran (30 mL) and add N-ethoxycarbonyl-2-ethoxy-1,2-dihydroquinoline (EEDQ) (469 mg). Stir overnight at room temperature under a nitrogen atmosphere. Evaporate the solvent in vacuo, partition between ethyl acetate and dilute hydrochloric acid. Separate the organic phase, wash with 5% sodium bicarbonate solution, water and brine. Dry (Na$_2$SO$_4$), evaporate the solvent in vacuo and purify and separate the isomers by silica gel chromatography to give the separate isomeric title compounds.

Scheme B, step c: [3R-[3α,6α,(S*),9aα]]-6-amino-octahydro-5-oxothiazolo[3,2-a][1,4]oxazepine-3-carboxylic acid Dissolve ethyl [3R-[3α,6α,(S*),9aα]]-6-[benzyloxycarbonylamino]octahydro-5-oxothiazolo[3,2-a][1,4]oxazepine-3-carboxylate (21.7 mmol) in ethanol (150 mL. Add 1N lithium hydroxide (50 mL) and stir overnight at room temperature. Concentrate in vacuo. Partition between ethyl acetate and 6N hydrochloric acid. Separate the organic phase and wash with brine. Dry (MgSO$_4$) and evaporate the solvent in vacuo to give [3R-[3α,6α,(S*),9aα]]-6-[benzyloxycarbonylamino]octahydro-5-oxothiazolo[3,2-a][1,4]oxazepine-3-carboxylic acid.

Mix [3R-[3α,6α,(S*),9aα]]-6-[benzyloxycarbonylamino]octahydro-5-oxothiazolo[3,2-a][1,4]oxazepine-3-carboxylic acid (27.7 mmol), trifluoroacetic acid (75 mL) and anisole (5 mL). Stir at room temperature overnight. Pour onto water and carefully neutralize with solid sodium hydrogen carbonate. Extract into ethyl acetate (2×), wash with brine and dry (MgSO$_4$). Evaporate the solvent in vacuo and purify by chromatography to give the title compound.

Scheme A, step a: [3R-[3α,6α,(S*),9aα]]-6-[[1-Oxo-2(R)-bromo-3-phenylpropyl]amino]octahydro-5-oxothiazolo[3-2-a][1,4]oxazepine-3-carboxylic acid Mix 3-phenyl-2(R)-bromopropionic acid (1.0 mmol) and [3R-[3α,6α,(S*),9aα]]-6-amino-octahydro-5-oxothiazolo[3,2-a][1,4]oxazepine-3-carboxylic acid (1.0 mmol) in methylene chloride (6 mL). Add EEDQ (247 mg, 1.0 mmol). Stir for 15 hours at ambient temperature under argon atmosphere. Dilute with ethyl acetate (25 mL) and wash with 5% sulfuric acid (15 mL), then saturated sodium hydrogen carbonate (15 mL). Dry (Na$_2$SO$_4$), concentrate in vacuo and purify by silica gel chromatography to yield the title compound.

Scheme A, step b: [3R-[3α,6α,(S*),9aα]]-6-[[1-Oxo-2(S)-acetylthio-3-phenylpropyl]amino]octahydro-5-oxothiazolo[3-2-a][1,4]oxazepine-3-carboxylic acid Dissolve thiolacetic acid (0.10 mL, 1.4 mmol) in methanol (5 mL) and treat with cesium carbonate (228 mg, 0.70 mmol). Stir the yellow solution for 30 minutes then evaporate the solvent in vacuo. Dilute the resulting cesium salt with dimethylformamdie (10 mL) and treat with a solution of [3R-[3α,6α,(S*),9aα]]-6-[[1-Oxo-2(R)-bromo-3-phenylpropyl]amino]octahydro-5-oxothiazolo[3-2-a][1,4]oxazepine-3-carboxylic acid (1.0 mmol) in tetrahydrofuran (6 mL). Stir at room temperature for 2 hours, evaporate the solvent in vacuo and partition between ethyl acetate (75 mL) and brine (50 mL). Dry the organic phase (Na$_2$SO$_4$), evaporate the solvent in vacuo and purify by chromatography to give the title compound.

EXAMPLE 5

[3R-[3α,6α,(S*),9aα]]-6-[[1-Oxo--2(S)-thio-3-phenylpropyl]amino]octahydro-5-oxothiazolo[3-2-a][1,4]oxazepine-3-carboxylic acid

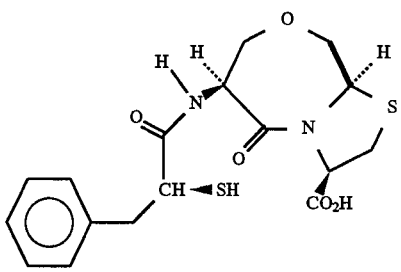

Dissolve [3R-[3α,6α,(S*),9aα]]-6-[[1-Oxo-2(S)-acetylthio-3-phenylpropyl]amino]octahydro-5-oxothiazolo[3-2-a][1,4]oxazepine-3-carboxylic acid (0.145 mmol) is degassed methanol (3 mL) and tetrahydrofuran (2 mL), cool in an ice bath and add lithium hydroxide (0.6 mL of a 1M solution, 0.6 mmol). Stir the reaction mixture for 3 hours and add 1N hydrochloric acid. Partition between methylene chloride (75 mL) and water (25 mL). Dry ($Na_2SO_4$), evaporate the solvent in vacuo and purify by chromatography to give the title compound.

EXAMPLE 6

[3R-[3α,6α,(S*),9aα]]-6-[[1-Oxo-2-(S)-acetylthio-3-phenypropyl]amino]octahydro-5-oxo-oxazolo[3-2-a]azepine-3-carboxylic acid

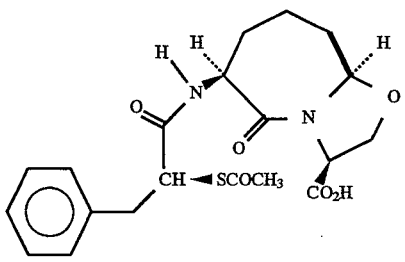

Scheme B, step a: Ethyl 2-(4'-carboxy-4-phthalimidobutyl)-4(R)-oxazolidinecarboxylate Dissolve L-serine ethyl ester (12.7 mmol) in tetrahydrofurn (120 mL) and add 5-formyl-2(S)-phthalimidopentanoic acid (12.7 mmol). Place under a nitrogen atmosphere and stir for 3 hours. Evaporate the solvent in vacuo, dissolve the residue in chloroform and wash with water (2×30 mL). Combine the aqueous extracts and extract with chloroform (2×30 mL). Combine all organic extracts, dry ($Na_2SO_4$) and evaporate the solvent in vacuo to give the title compound.

Scheme B, step b: Ethyl [3R-[3α,6α,(S*),9aα]]-6-phthalimidooctahydro-5-oxo-oxazolo[3,2-a]azepine-3-carboxylate and Ethyl [3R-[3α,6α,(S*),9aβ]]-6-phthalimidooctahydro-5-oxo-oxazolo[3,2-a]azepine-3-carboxylate Dissolve ethyl 2-(4'-carboxy-4-phthalimidobutyl)-4(R)-oxazolidinecarboxylate (12.7 mmol) in tetrahydrofuran (30 mL) and add N-ethoxycarbonyl-2-ethoxy-1,2-dihydroquinoline (EEDQ) (469 mg). Stir overnight at room temperature under a nitrogen atmosphere. Evaporate the solvent in vacuo, partition between ethyl acetate and dilute hydrochloric acid. Separate the organic phase, wash with 5% sodium bicarbonate solution, water and brine. Dry ($Na_2SO_4$), evaporate the solvent in vacuo and purify and separate the isomers by silica gel chromatography to give the separate isomeric title compounds.

Scheme B, step c: [3R-[3α,6α,(S*),9aα]]-6-amino-octahydro-5-oxo-oxazolo[3,2-a]azepine-3-carboxylic acid Dissolve ethyl [3R-[3α,6α,(S*),9aα]]-6-phthalimidooctahydro-5-oxo-oxazolo[3,2-a][1,4]oxzepine-3-carboxylate (0.517 mmol) in methanol (5 mL) and treat with hydrazine monohydrate (1.1 mL of a 1M solution in methanol, 1.1 mmol). Stir at room temperature for 44 hours, evaporate the solvent in vacuo and slurry the residue in methylene chloride (10 mL). Filter and evaporate the solvent in vacuo to give ethyl [3R-[3α,6α,(S*),9aα]]-6-amino-octahydro-5-oxo-oxazolo[3,2-a][1,4]oxepine-3-carboxylate.

Dissolve ethyl [3R-[3α,6α,(S*),9aα]]-6-phthalimidooctahydro-5-oxo-oxazolo[3,2-a]azepine-3-carboxylate (21.7 mmol) in ethanol (150 mL. Add 1N lithium hydroxide (50 mL) and stir overnight at room temperature. Reflux for 1 hour and concentrate in vacuo. Partition between ethyl acetate and 6N hydrochloric acid. Separate the organic phase and wash with brine. Dry ($MgSO_4$) and evaporate the solvent in vacuo to give the title compound.

Scheme A, step a: [3R-[3α,6α,(S*),9aα]]-6-]]1-Oxo-2(R)-bromo-3-phenylpropyl]amino]octahydro-5-oxo-oxazolo[3-2-a]azepine-3-carboxylic acid Mix 3-phenyl-2(R)-bromopropionic acid (1.0 mmol) and [3R-[3α,6α,(S*),9aα]]-6-amino-octahydro-5-oxo-oxazolo[3,2-a]azepine-3-carboxylic acid (1.0 mmol) in methylene chloride (6 mL). Add EEDQ (247 mg, 1.0 mmol). Stir for 15 hours at ambient temperature under argon atmosphere. Dilute with ethyl acetate (25 mL) and wash with 5% sulfuric acid (15 mL), then saturated sodium hydrogen carbonate (15 mL). Dry ($Na_2SO_4$), concentrate in vacuo and purify by silica gel chromatography to yield the title compound.

Scheme A, step b: [3R-[3α,6α,(S*),9aα]]-6-[[1-Oxo-2(S)-acetylthio-3-phenylpropyl]amino]octahydro-5-oxo-oxazolo[3-2-a]azepine-3-carboxylic acid Dissolve thiolacetic acid (0.10 mL, 1.4 mmol) in methanol (5 mL) and treat with cesium carbonate (228 mg, 0.70 mmol). Stir the yellow solution for 30 minutes then evaporate the solvent in vacuo. Dilute the resulting cesium salt with dimethylformamdie (10 mL) and treat with a solution of [3R-[3α,6α,(S*),9aα]]-6-[[1-Oxo-2(R)-bromo-3-phenylpropyl]amino]octahydro-5-oxo-oxazolo[3-2-a]azepine-3-carboxylic acid (1.0 mmol) in tetrahydrofuran (6 mL). Stir at room temperature for 2 hours, evaporate the solvent in vacuo and partition between ethyl acetate (75 mL) and brine (50 mL). Dry the organic phase ($Na_2SO_4$), evaporate the solvent in vacuo and purify by chromatography to give the title compound.

EXAMPLE 7

[3R-[3α,6α,(S*),9aα]]-6-[[1-Oxo-2(S)-thio-3-phenylpropyl]amino]octahydro-5-oxo-oxazolo[3-2-a]azepine-3-carboxylic acid

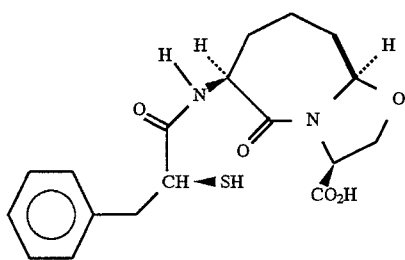

Dissolve [3R-[3α,6α,(S*),9aα]]-6-[[1-oxo-2(S)-acetylthio-3-phenylpropyl]amino]octahydro-5-oxo-oxazolo[3-2-a]azepine-3-carboxylic acid (0.145 mmol) in degassed methanol (3 mL) and tetrahydrofuran (2 mL), cool in an ice bath and add lithium hydroxide (0.6 mL of a 1M solution, 0.6 mmol). Stir the reaction mixture for 3 hours and add 1N hydrochloric acid. Partition between methylene chloride (75 mL) and water (25 mL). Dry (Na₂SO₄), evaporate the solvent in vacuo and purify by chromatography to give the title compound.

EXAMPLE 8

[3R-[3α,6α,(S*),9aα]]-6-[[1-Oxo-2(S)-acetylthio-3-phenylpropyl]amino]octahydro-5-oxothiazolo[3-2-a]azepine-3-carboxylic acid

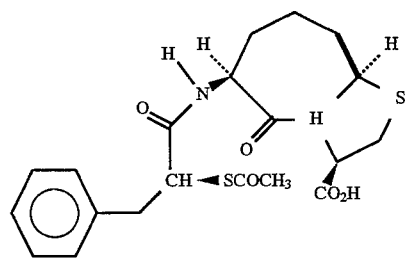

Scheme A, step a:[3R-[3α,6α,(S*),9aα]]-6-[[1-Oxo-2(R)-bromo-3-phenylpropyl]amino]octahydro-5-oxothiazolo[3-2-a]azepine-3-carboxylic acid Mix 3-phenyl-2(R)-bromopropionic acid (1.0 mmol) and [3R-(3α,6α,9aβ)-6-aminooctahydro-5-oxo-thiazolo[3,2-a]azepine-3-carboxylic acid (1.0 mmol) in methylene chloride (6 mL). Add EEDQ (247 mg, 1.0 mmol). Stir for 15 hours at ambient temperature under argon atmosphere. Dilute with ethyl acetate (25 mL) and wash with 5% sulfuric acid (15 mL), then saturated sodium hydrogen carbonate (15 mL). Dry (Na₂SO₄), concentrate in vacuo and purify by silica gel chromatography to yield the title compound.

Scheme A, step b: [3R-[3α,6α,(S*),9aα]]-6-[[1-Oxo-2(S)-acetylthio-3-phenylpropyl]amino]octahydro-5-oxothiazolo[3-2-a]azepine-3-carboxylic acid Dissolve thiolacetic acid (0.10 mL, 1.4 mmol) in methanol (5 mL) and treat with cesium carbonate (228 mg, 0.70 mmol). Stir the yellow solution for 30 minutes then evaporate the solvent in vacuo. Dilute the resulting cesium salt with dimethylformamide (10 mL) and treat with a solution of [3R-[3α,6α,(S*),9aα]]-6-[[1-Oxo-2(R)-bromo-3-phenylpropyl]amino]octahydro-5-oxothiazolo[3-2-a]azepine-3-carboxylic acid (1.0 mmol) in tetrahydrofurn (6 mL). Stir at room temperature for 2 hours, evaporate the solvent in vacuo and partition between ethyl acetate (75 mL) and brine (50 mL). Dry the organic phase (Na₂SO₄), evaporate the solvent in vacuo and purify by chromatography to give the title compound.

EXAMPLE 9

[3R-[3α,6α,(S*),9aα]]-6-[[1-Oxo-2(S)-thio-3-phenylpropyl]amino]octahydro-5-oxothiazolo[3-2-a]azepine-3-carboxylic acid

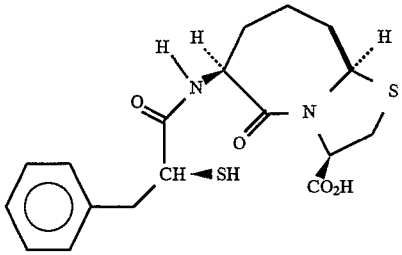

Dissolve [3R-[3α,6α,(S*),9aα]]-6-[[1-Oxo-2(S)-acetylthio-3-phenylpropyl]amino]octahydro-5-oxothiazolo[3-2-a]azepine-3-carboxylic acid (0.145 mmol) in degassed methanol (3 mL) and tetrahydrofuran (2 mL), cool in an ice bath, place under a nitrogen atmosphere and add lithium hydroxide (0.6 mL of a 1M solution, 0.6 mmol). Stir the reaction mixture for 3 hours and add 1N hydrochloric acid. Partition between methylene chloride (75 mL) and water (25 mL). Dry (Na₂SO₄), evaporate the solvent in vacuo and purify by chromatography to give the title compound.

The following compounds can be prepared by procedures analogous to those described above in Examples 1–9:

[3R-[3α,6α,(S*),9aα]]6-[[1-Oxo-2(S)-acetylthio-3-phenylpropyl]amino]octahydro-5-oxo-oxazolo[3-2-a][1,4]oxazepine-3-carboxylic acid;

[3R-[3α,6α,(S*),9aα]]-6-[[1-Oxo-2(S)-(4-morpholino)acetylthio-3-phenylpropyl]amino]octahydro-5-oxo-oxazolo[3-2-a][1,4]oxazepine-3-carboxylic acid;

[3R-[3α,6α,(S*),9aα]]-6-[[1-Oxo-2(S)-thio-3-phenylpropyl]amino]octahydro-5-oxo-oxazolo[3-2-a][1,4]oxazepine-3-carboxylic acid

[3R-[3α,6α,(S*),9aα]]-6-[[1-Oxo-2(S)-acetylthio-3-phenylpropyl]amino]octahydro-5-oxo-oxazolo[3-2-a][1,4]thiazepine-3-carboxylic acid;

[3R-[3α,6α,(S*),9aα]]-6-[[1-Oxo-2(S)-(4-morpholino)acetylthio-3-phenylpropyl]amino]octahydro-5-oxo-oxoazolo[3-2-a][1,4]thiazepine-3-carboxylic acid;

[3R-[3α,6α,(S*),9aα]]-6-[[1-Oxo-2(S)-thio-3-phenylpropyl]amino]octahydro-5-oxothiazolo[3-2-a][1,4]thiazepine-3-carboxylic acid;

[3R-[3α,6α,(S*),9aα]]-6-[[1-Oxo-2(S)-(4-morpholino)acetylthio-3-phenylpropyl]amino]octahydro-5-oxothiazolo[3-2-a][1,4]oxazepine-3-carboxylic acid;

[3R-[3α,6α,(S*),9aα]]-6-[[1-Oxo-2(S)-(4-morpholino)acetylthio-3-phenylpropyl]amino]octahydro-5-oxo-oxazolo[3-2-a]azepine-3-carboxylic acid; and

[3R-[3α,6α,(S*),9aα]]-6-[[1-Oxo-2(S)-(4-morpholino)acetylthio-3-phenylpropyl]amino]octahydro-5-oxothiazolo[3-2-a]azepine-3-carboxylic acid.

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram of body weight per day (mg/kg/day) to about 20 mg/kg/day. A daily dose of from about 0.1 mg/kg to about 10 mg/kg is preferred.

In addition, the present invention further provides a method of inhibiting ACE in a patient in need thereof comprising administering to said patient an effective ACE inhibitory amount of a compound of Formula (I). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyperaldosteronemic effects caused thereby. An effective ACE inhibitory amount of a compound of Formula (I) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound of Formula (I) is that amount which is effective in inhibiting smooth cell proliferation in a patient in need thereof which results, for example, in a reduced myointimal thickening after vascular injury. An effective smooth cell proliferation inhibitory amount and an effective smooth cell proliferation inhibitory dose are the same as that described above for an effective enkephalinase inhibitory amount and dose.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising and effective amount of a compound of Formula (I) in admixture of otherwise in association with one or more pharmaceutically acceptable carriers or excipients.

The pharmaceutical compositions or medicaments are prepared in a manner well known in the pharmaceutical art.

The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application.

The compounds of Formula (I) wherein $R_1$ is acetyl or a group of the formula

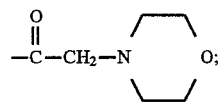

$R_2$ is an Ar—Y group wherein Ar is phenyl, 4,5-methylenedioxyphenyl or 2-benzofuranyl and Y is —CH$_2$—; A is —S— or —CH$_2$—; B is —S— and R is hydrogen, ethyl or benzyl are preferred.

It is, of course, understood that the compounds of Formula (I) may exist in a variety of isomeric configurations including structural as well as stereo isomers. It is further understood that the present invention encompasses those compounds of Formula (I) in each of their various structural and stereo isomeric configurations as individual isomers and as mixtures of isomers.

The following specific compounds of Formula (1) are particularly preferred in the end-use application of the compounds of the present invention:

[3R-[3α,6α,(S*),9aα]]-6-[[1-Oxo-2(S)-acetylthio-3-phenylpropyl]amino]octahydro-5-oxothiazolo[3-2-a][1,4]thiazepine-3-carboxylic acid;

[3R-[3α,6α,(S*),9aα]]-6-[[1-Oxo-2(S)-thio-3-phenylpropyl]amino]octahydro-5-oxothiazolo[3-2-a][1,4]thiazepine-3-carboxylic acid;

[3R-[3α,6α,(S*),9aα]]-6-[[1-Oxo-2(S)-(4-morpholino)-acetylthio-3-phenylpropyl]amino]octahydro-5-oxothiazolo[3-2-a][1,4]thiazepine-3-carboxylic acid;

[3R-[3α,6α,(S*),9aα]]-6-[[1-Oxo-2(S)-acetylthio-3-phenylpropyl]amino]octahydro-5-oxothiazolo[3-2-a][1,4]oxazepine-3-carboxylic acid;

[3R-[3α,6α,(S*),9aα]]-6-[[1-Oxo-2(S)-thio-3-phenylpropyl]amino]octahydro-5-oxothiazolo[3-2-a][1,4]oxazepine-3-carboxylic acid;

[3R-[3α,6α,(S*),9aα]]-6-[[1-Oxo-2(S)-acetylthio-3-phenylpropyl]amino]octahydro-5-oxo-oxazolo[3-2-a]azepine-3-carboxylic acid;

[3R-[3α,6α,(S*),9aα]]-6-[[1-Oxo-2(S)-thio-3-phenylpropyl]amino]octahydro-5-oxo-oxazolo[3-2-a]azepine-3-carboxylic acid;

[3R-[3α,6α,(S*),9aα]]-6-[[1-Oxo-2(S)-acetylthio-3-phenylpropyl]amino]octahydro-5-oxothiazolo[3-2-a]azepine-3-carboxylic acid;

[3R-[3α,6α,(S*),9aα]]-6-[[1-Oxo-2(S)-thio-3-phenylpropyl]amino]octahydro-5-oxothiazolo[3-2-a]azepine-3-carboxylic acid;

[3R-[3α,6α,(S*),9aα]]-6-[[1-Oxo-2(S)-acetylthio-3-phenylpropyl]amino]octahydro-5-oxo-oxazolo[3-2-a][1,4]oxazepine-3-carboxylic acid;

[3R-[3α,6α,(S*),9aα]]-6-[[1-Oxo-2(S)-thio-3-phenylpropyl]amino]octahydro-5-oxo-oxazolo[3-2-a][1,4]oxazepine-3-carboxylic acid

[3R-[3α,6α,(S*),9aα]]-6-[[1-Oxo-2(S)-acetylthio-3-phenylpropyl]amino]octahydro-5-oxo-oxazolo[3-2-a][1,4]thiazepine-3-carboxylic acid;

[3R-[3α,6α,(S*),9aα]]-6-[[1-Oxo-2(S)-(4-morpholino) acetylthio-3-phenylpropyl]amino]octahydro-5-oxo-oxazolo[3-2-a][1,4]thiazepine-3-carboxylic acid;

[3R-[3α,6α,(S*),9aα]]-6-[[1-Oxo-2(S)-thio-3-phenylpropyl]amino]octahydro-5-oxothiazolo[3-2-a][1,4]thiazepine-3-carboxylic acid;

[3R-[3α,6α,(S*),9aα]]-6-[[1-Oxo-2(S)-(4-morpholino)acetylthio-3-phenylpropyl]amino]octahydro-5-oxothiazolo[3-2-a][1,4]oxazepine-3-carboxylic acid;

[3R-[3α,6α,(S*),9aα]]-6-[[1-Oxo-2(S)-(4-morpholino)acetylthio-3-phenylpropyl]amino]octahydro-5-oxo-oxazolo[3-2-a][1,4]oxazepine-3-carboxylic acid;

[3R-[3α,6α,(S*),9aα]]-6-[[1-Oxo-2(S)-(4-morpholino)
  acetylthio-3-phenylpropyl]amino]octahydro-5-oxo-
  oxazolo[3-2-a]azepine-3-carboxylic acid; and
[3R-[3α,6α,(S*),9aα]]-6-[[1-Oxo-2(S)-(4-morpholino)
  acetylthio-3-phenylpropyl]amino]octahydro-5-
  oxothiazolo[3-2-a]azepine-3-carboxylic acid.

The following studies illustrate the utility of the compounds of the present invention as enkephalinase inhibitors and as ACE inhibitors.

Enkephalinase is partially purified from rat kidney. The enzyme is extracted from the microvilli fraction by using Triton X-100 according to the method of Malfroy and Schwartz [*J. Biol. Chem.* 259, 14365–14370 (1984)] or by using a proteolytic treatment according to the method of Almenoff and Orlowski [*Biochem.* 22, 590–599 (1983)]. The enzyme is further purified by anion exchange chromatography (Mono Q™ column, Pharmacia) using a Pharmacia FPLC system. The enzyme activity may be measured by the fluorometric methods of Florentin et al. [*Anal. Biochem.* 141, 62–69 (1984)] or of Almenoff and Orlowski [*J. Neurochemistry* 42, 151–157 (1984)]. The enzyme is assayed in 50 mM HEPES buffer (pH 7.4) in a 3.0 mL reaction volume containing 12 μM of the substrate dansyl-D-AlaGly(p-nitro)PheGly ($K_m$=40 μM) at 25° C. The substrate (and inhibitor) is added from a concentrated stock solution in DMSO (up to 0.1 mL DMSO final volume). The enzyme in a small volume (approximately 0.1 μg of FPLC purified protein) is added to initiate the reaction and the rate of fluorescence increase is recorded continuously using a fluorometer (excitation at 339 nm, emission at 562 nm).

The enzymatic activity of ACE is monitored using the spectrophotometric substrate described by Holmquist et al. [*Anal. Biochem.* 95, 540–548 (1979)] and the buffer system described by Ryan [*Methods of Enzymatic Analysis*, 3rd ed., H. U. Bergmeyer, editor; vol. V, Verlag Chemie, Weinheim, 1983, pp. 20–34].

What is claimed is:

1. A compound of the formula

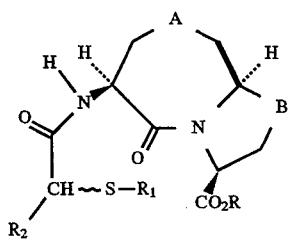

wherein
R is hydrogen, a $C_1$-$C_4$ alkyl or an Ar—Y— group wherein Y is $C_0$-$C_4$ alkyl, —$CH_2$O—C(O)C($CH_3$)$_3$ or diphenylmethyl; $R_1$ is hydrogen, acetyl, —$CH_2$O—C(O)C($CH_3$)$_3$ or benzoyl or a group of the formula

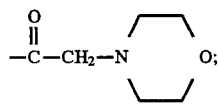

$R_2$ is hydrogen, $C_1$-$C_8$ alkyl, —$CH_2OCH_2CH_2OCH_3$ or an Ar—Y— group;
A is —$CH_2$—, —O—, or —S—; ev1 B is —S— or —O—; or
the pharmaceutically acceptable salts thereof.

2. A compound according to claim 1 wherein A is —S—.

3. A compound according to claim 2 wherein B is —S—.

4. A compound according to claim 3 wherein $R_2$ is phenylmethyl.

5. A compound according to claim 4 wherein $R_1$ is acetyl.

6. A compound according to claim 4 wherein $R_1$ is a group of the formula

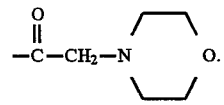

7. A compound according to claim 1 wherein A is —$CH_2$—.

8. A compound according to claim 7 wherein B is —S—.

9. A compound according to claim 8 wherein $R_2$ is phenylmethyl.

10. A compound according to claim 9 wherein $R_1$ is acetyl.

11. A compound according to claim 10 wherein $R_1$ is a group of the formula

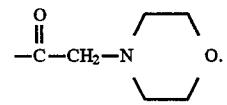

12. A compound of claim 1 wherein the compound is [3R-[3α,6α,(S*),9aα]]-6-[[1-Oxo-2(S)-acetylthio-3-phenylpropyl]amino]octahydro-5-oxothiazolo[3-2-a][1,4]thiazepine-3-carboxylic acid.

13. A compound of claim 1 wherein the compound is [3R-[3α,6α,(S*),9aα]]-6-[[1-Oxo-2(S)-(4-morpholino)-acetylthio-3-phenylpropyl]amino]octahydro-5-oxothiazolo[3-2-a][1,4]thiazepine-3-carboxylic acid.

14. A compound of claim 1 wherein the compound is [3R-[3α,6α,(S*),9aα]]-6-[[1-Oxo-2(S)-acetylthio-3-phenylpropyl]amino]octahydro-5-oxo-oxazolo[3-2-a]azepine-3-carboxylic acid.

15. A compound of claim 1 wherein the compound is [3R-[3α,6α,(S*),9aα]]-6-[[1-Oxo-2(S)-acetylthio-3-phenylpropyl]amino]octahydro-5-oxothiazolo[3-2-a]azepine-3-carboxylic acid.

16. A compound of claim 1 wherein the compound is [3R-[3α,6α,(S*),9aα]]-6-[[1-Oxo-2(S)-acetylthio-3-phenylpropyl]amino]octahydro-5-oxo-oxazolo[3-2-a][1,4]thiazepine-3-carboxylic acid.

17. A compound of claim 1 wherein the compound is [3R-[3α,6α,(S*),9aα]]-6-[[1-Oxo-2(S)-(4-morpholino)acetylthio-3-phenylpropyl]amino]octahydro-5-oxo-oxazolo[3-2-a][1,4]thiazepine-3-carboxylic acid.

18. A compound of claim 1 wherein the compound is [3R-[3α,6α,(S*),9aα]]-6-[[1-Oxo-2(S)-(4-morpholino)acetylthio-3-phenylpropyl]amino]octahydro-5-oxo-oxazolo[3-2-a]azepine-3-carboxylic acid.

19. A compound of claim 1 wherein the compound is [3R-[3α,6α,(S*),9aα]]-6-[[1-Oxo-2(S)-(4-morpholino)acetylthio-3-phenylpropyl]amino]octahydro-5-oxothiazolo[3-2-a]azepine-3-carboxylic acid.

20. A method of inhibiting enkephalinase in a patient in need thereof comprising administering to said patient an effective enkephalinase inhibitory amount of a compound of the formula

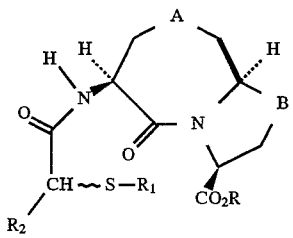

wherein

R is hydrogen, a $C_1$–$C_4$ alkyl or an Ar—Y— group wherein Y is $C_0$–$C_4$ alkyl, —$CH_2O$—$C(O)C(CH_3)_3$ or diphenylmethyl;

$R_1$ is hydrogen, acetyl, —$CH_2O$—$C(O)C(CH_3)_3$ or benzoyl or a group of the formula

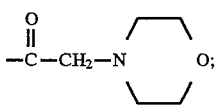

$R_2$ is hydrogen, $C_1$–$C_8$ alkyl, —$CH_2OCH_2CH_2OCH_3$ or an Ar—Y— group;

A is —$CH_2$—, —O—, or —S—;

B is —S— or —O—; or the pharmaceutically acceptable salts thereof.

21. A method according to claim 20 wherein the patient is in need of an endorphin- or enkephalin-mediated analgesic effect.

22. A method according to claim 20 wherein the patient is in need of an ANP-mediated hypotensive effect.

23. A method according to claim 20 wherein the patient is in need of an ANP-mediated diuretic effect.

24. A method according to claim 20 wherein the patient is suffering from congestive heart failure.

25. A method according to claim 20 wherein the patient is suffering from irritable bowel syndrome.

26. A method of inhibiting ACE in a patient in need thereof comprising administering to said patient an effective ACE inhibitory amount of a compound of the formula

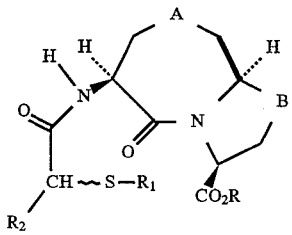

wherein

R is hydrogen, a $C_1$–$C_4$ alkyl or an Ar—Y— group wherein Y is $C_0$–$C_4$ alkyl, —$CH_2O$—$C(O)C(CH_3)_3$ or diphenylmethyl;

$R_1$ is hydrogen, acetyl, —$CH_2O$—$C(O)C(CH_3)_3$ or benzoyl or a group of the formula

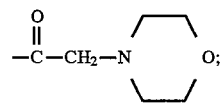

$R_2$ is hydrogen, $C_1$–$C_8$ alkyl, —$CH_2OCH_2CH_2OCH_3$ or an Ar—Y— group;

A is —$CH_2$—, —O—, or —S—;

B is —S— or —O—; or the pharmaceutically acceptable salts thereof.

27. A method according to claim 26 wherein the patient is in need of a hypotensive effect.

28. A method according to claim 26 wherein the patient is in need of a cognition enhancing effect.

29. A method according to claim 26 wherein the patient is suffering from congestive heart failure.

30. A method of inhibiting smooth cell proliferation in a patient in need thereof comprising administering to said patient an effective smooth cell proliferation inhibitory amount of a compound of the formula

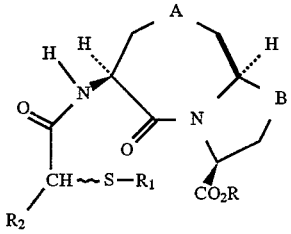

wherein

R is hydrogen, a $C_1$–$C_4$ alkyl or an Ar—Y— group wherein Y is $C_0$–$C_4$ alkyl, —$CH_2O$—$C(O)C(CH_3)_3$ or diphenylmethyl;

$R_1$ is hydrogen, acetyl, —$CH_2O$—$C(O)C(CH_3)_3$ or benzoyl or a group of the formula

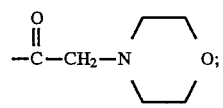

$R_2$ is hydrogen, $C_1$–$C_8$ alkyl, —$CH_2OCH_2CH_2OCH_3$ or an Ar—Y— group;

A is —$CH_2$—, —O—, or —S—;

B is —S— or —O—; or the pharmaceutically acceptable salts thereof.

31. A composition comprising an 0.001% to 75% composition by weight of a compound of claim 1 in admixture or otherwise in association with an inert carrier.

32. A pharmaceutical composition comprising 0.001% to 75% composition by weight of a compound of claim 1 in admixture or otherwise in association with one or more pharmaceutically acceptable carriers or excipients.

* * * * *